US007947492B2

(12) United States Patent
Niehaus (10) Patent No.: US 7,947,492 B2
(45) Date of Patent: May 24, 2011

(54) DEVICE IMPROVING THE DETECTION OF A LIGAND

(75) Inventor: Gary D. Niehaus, Kent, OH (US)

(73) Assignee: Northeastern Ohio Universities College of Medicine, Rootstown, OH (US)

( * ) Notice: Subject to any disclaimer, the term of this patent is extended or adjusted under 35 U.S.C. 154(b) by 11 days.

(21) Appl. No.: 12/194,829

(22) Filed: Aug. 20, 2008

(65) Prior Publication Data

US 2010/0047920 A1 Feb. 25, 2010

(51) Int. Cl.
*C12M 1/34* (2006.01)
(52) U.S. Cl. ............... 435/288.7; 435/283.1; 435/286.5; 435/287.1; 435/288.3; 422/50; 422/55; 422/61; 422/82.05; 422/82.11
(58) Field of Classification Search ............... 435/288.7, 435/283.1, 286.5, 287.1, 288.3; 422/50, 422/55, 61, 82.05, 82.11
See application file for complete search history.

(56) References Cited

U.S. PATENT DOCUMENTS

| | | | | |
|---|---|---|---|---|
| 2,645,463 | A | 7/1953 | Stearns | |
| 3,306,111 | A * | 2/1967 | Ferrin | 73/863.73 |
| 4,165,644 | A * | 8/1979 | Brandt et al. | 73/864.83 |
| 4,604,364 | A | 8/1986 | Kosak | |
| 4,673,657 | A | 6/1987 | Christian | |
| 4,794,806 | A * | 1/1989 | Nicoli et al. | 73/863.01 |
| 4,943,525 | A | 7/1990 | Dawson | |
| 5,100,626 | A | 3/1992 | Levin | |
| 5,116,576 | A | 5/1992 | Stanley | |
| 5,149,626 | A | 9/1992 | Fleming | |
| 5,447,837 | A | 9/1995 | Urnovitz | |
| 5,514,111 | A * | 5/1996 | Phelps | 604/248 |
| 5,593,838 | A | 1/1997 | Zanzucchi et al. | |
| 5,596,434 | A | 1/1997 | Walba et al. | |
| 5,620,252 | A | 4/1997 | Maurer | |
| 5,650,327 | A | 7/1997 | Copeland et al. | |
| 5,652,149 | A | 7/1997 | Mileaf et al. | |
| 5,688,047 | A | 11/1997 | Signer | |
| 5,756,696 | A | 5/1998 | Gray et al. | |
| 5,780,248 | A | 7/1998 | Milchanoski et al. | |

(Continued)

FOREIGN PATENT DOCUMENTS

DE 3617710 12/1986

(Continued)

OTHER PUBLICATIONS

Shiyanovskii, et al., "Computer Simulations and Fluorescenses Confocal Polarizing Microscopy of Structures in Cholesteric Liquid Crystals", Defects in Liquid Crystals, dates 2001, vol. 43, pp. 229-270.

(Continued)

*Primary Examiner* — Melanie J Yu
(74) *Attorney, Agent, or Firm* — Calfee, Halter & Griswold LLP (57) ABSTRACT

A device and method is disclosed for improving the detection of a ligand by a receptor by concentrating microbes by removing particulates from fluid-borne samples and/or causing selective aggregation of concentrated microbes. The device may be configured as a multipath valve capable purifying/concentrating a sample in one orientation and delivering the concentrated sample in another orientation. In one embodiment, the device includes a body that defines a plurality of chambers and pathways and supports a pathogen capture unit that houses a receptor that exhibits specificity for a ligand. In another embodiment, the capture unit houses a plurality of antibody coated generally spherical particles capable of binding to a ligand.

35 Claims, 9 Drawing Sheets

U.S. PATENT DOCUMENTS

| | | | |
|---|---|---|---|
| 5,826,977 A | 10/1998 | Fowler et al. | |
| 5,826,981 A | 10/1998 | Fowler et al. | |
| 5,863,502 A | 1/1999 | Southgate et al. | |
| 5,864,641 A | 1/1999 | Murphy et al. | |
| 5,912,134 A | 6/1999 | Shartle | |
| 6,030,581 A | 2/2000 | Virtanen | |
| 6,043,067 A | 3/2000 | Lihme et al. | |
| 6,062,721 A | 5/2000 | King et al. | |
| 6,171,802 B1 | 1/2001 | Woolverton et al. | |
| 6,284,197 B1 | 9/2001 | Abbott et al. | |
| 6,302,134 B1 | 10/2001 | Kellogg et al. | |
| 6,303,389 B1 | 10/2001 | Levin et al. | |
| 6,319,468 B1 | 11/2001 | Sheppard, Jr. et al. | |
| 6,345,907 B1 | 2/2002 | Akay et al. | |
| 6,361,202 B1 | 3/2002 | Lee et al. | |
| 6,387,328 B1* | 5/2002 | Berndtsson | 422/73 |
| 6,468,807 B1 | 10/2002 | Svensson et al. | |
| 6,482,328 B1* | 11/2002 | Davidson et al. | 210/695 |
| 6,813,568 B2* | 11/2004 | Powell et al. | 702/31 |
| 6,836,326 B2 | 12/2004 | Hajduk et al. | |
| 7,060,225 B2 | 6/2006 | Niehaus | |
| 7,160,736 B2* | 1/2007 | Niehaus et al. | 436/525 |
| 7,267,957 B2* | 9/2007 | Woolverton et al. | 435/7.1 |
| 7,732,219 B2* | 6/2010 | Woolverton et al. | 436/525 |
| 7,811,811 B2* | 10/2010 | Niehaus | 435/288.7 |
| 2002/0052002 A1 | 5/2002 | Niehaus et al. | |
| 2002/0168511 A1 | 11/2002 | Schneider et al. | |
| 2004/0038408 A1 | 2/2004 | Abbott et al. | |
| 2006/0263246 A1* | 11/2006 | Berndtsson | 422/58 |
| 2007/0042489 A1 | 2/2007 | Niehaus | |
| 2007/0092868 A1 | 4/2007 | Woolverton et al. | |

FOREIGN PATENT DOCUMENTS

| | | |
|---|---|---|
| WO | 95/33803 | 12/1995 |
| WO | 02/079755 | 10/2002 |

OTHER PUBLICATIONS

Smalyukh, et al., "Three-Dimensional Imaging of Orientational Order by Fluorescense Confocal Polarizing Microscopy", Chemical Physics Letter, vol. 336, dated 2001, pp. 88-96.

Strosberg, et al., "Receptor-Based Assays", Current Opinion in Biotechnology, dated 1991, vol. 2, pp. 30-36.

Sutherland, et al., "Surface Effect Immunoassay", dated 1991, Stockton Press, pp. 515-542.

Ter Meulen, et al., "Detection of Lassa Virus Antinucleoprotein Immunoglobulin G (IgG) and IgM Antibodies by a Simple Recombinant Immunoblot Assay for Field Use", Journal of Clinical Microbiology, dated Nov. 1998, vol. 36, No. 11, pp. 3143-3148.

Vasilevskaya, et al., Chromonic Mesophases, Russian Chemical Reviews, dated 1989, vol. 58, pp. 904-916.

Winter, et al., Making Antibodies by Phage Display Technology, Annual Reviews Innunol, dated 1994, vol. 12, pp. 433-455.

Yamaguchi, et al., "Detection of Anti-Human T-Lymphotropic Virus Type I Antibody in Whole Blood by a Novel Counting Immunoassay", Clinical Chemistry, dated 2003, vol. 49, pp. 275-280.

Zamora, et al., "Chemiluminescent Immunoassay in Comparison with the Indirect ELISA as Reference Method for Detecting Salmonella Antibodies in Swine Meat Juice", Berliner and Munchener Tierarztliche Wochenshrift, dated 2002, vol. 115, pp. 369-380.

Shiyanowskii, et al., "Lyotropic Chromonic Liquid Crystals for Biological Sensing Applications", Mol. Cryst. Liq. Cryst, vol, 434, dated 2005, 259[587]-270[598].

Born, et al., Chapter XIV, "Optics of Crystals, The Dielectric Tensor of an Anisotropic Medium", Sixth Edition., Pergamon Press, dated 1980, pp. 665-718.

Brooks et al, "Specificity of Monoclonal Antibodies to Camplylobacter Jejuni Lipopolysaccharide Antigens", Immunoligical Investigations, dated 1998, vol. 27, pp. 257-265.

Buhrer-Sekula, et al., "The Use of Whole Blood in a Dipstick Assay for Detection of Antibodies to Mycobacterium Leprae: A Field Evaluation", FEMS Immunology and Medical Microbiology, dated 1998, vol. 21, pp. 197-201.

Collings, "Liquid Crystals:Nature's Delicate Phase of Matter", 2d Ed., Princeton Science Library, dated 1990, pp. 8-23.

Deng, et al., "Basis for Selection of Improved Carbohydrate-Binding Single-Chain Antibodies from Synthetic Gene Libraries", Proc. Natl. Acad. Sci, USA, dated 1995, vol. 92, pp. 992-4996.

Grabowska, et al., "Evaluation of Cost-Precision Rations of Different Strategies for ELISA Measurement of Serum Antibody Levels", Journal of Immunological Methods, dated 2002, vol, 271, pp. 1-15.

Griffiths, et al., "Human Anti-Self Antibodies with High Specificity from Phage Display Libraries", The EMBO Journal, dated 1993, vol. 12, No. 2, pp. 725-734.

Gupta, et al., "Design of Surfaces for Patterned Alignment of Liquid Crystals on Planar and Curved Substrates", Science, dated 1997, vol, 276, pp. 1553-1536.

Gupta, et al., "Optical Amplification of Ligand-Receptor Binding Using Liquid Crystals", Science, American Association for the Advancement of Science, dated 1998, vol. 279, pp. 2077-2080.

Halfon, et al., Serological Response to Infection with Different Isolates of Hepatitis C Virus, Journal of Viral Hepatitis, dated 2002, vol. 9, pp. 438-442.

Harlaw, et al. "Antibodies Laboratory Manual", Cold Spring Harbor Laboratory, dated 1988, Chapter 6, pp. 141-142.

Hartshorne, et al., "Mesomorphism in the System Disodiium Chromoglycate-Water" Molecular Crystals and Liquid Crystals, dated 1973, vol. 23, pp. 343-368.

Hasui, et al., "Low-Birefringence Thermally and Environmentally Stable Slab Waveguide Planarized by Hot Embossing", Japanese Journal of Applied Physics, vol. 43, No. 4B, dated 2004, pp. 2341-2345.

Helm, et al., "Measurement of Ligand-Receptor Interactions", Proceedings of the National Academy of Sciences of the United States, dated 1991, vol. 88, pp. 8169-8173.

Hollinger, "Diabodies:Small Bivalent and Bispecific Antibody Fragments", Proceedings of the National Academy of Sciences of the United States, dated 1998, vol. 90, pp. 6444-6448.

Jerome, "Surface effects and anchoring in Liquid Crystals", Rep. Prog. Phys., dated 2001, vol. 54, pp. 391-452.

Jones, "Life in the 21st century—A Vision for All", S. Afr. Med. J., dated 1998, vol. 88, Chapter 6, pp. 674.

Lee, et al., "Phase Diagram and Thermodynamic Properties of Disodium Cromoglycate-Water Lyomesophases", Molecular Crystals and Liquid Crystals, dated 1983, vol. 91, pp. 53.

Lydon, "Chromonic Liquid Crystal Phases", Current Opinion in Colloid & Interface Science, dated 1998, vol. 3. pp. 458-466.

Lydon, "Chromonics" Handbook of Liquid Crystals, Chapter XVIII, dated 1998, vol. 2B, pp. 981-1007.

Marks, et al., "By-Passing Immunization Human Antibodies from V-Gene Libraries Displayed on Phage", J. Mol. Biol., dated 1991, vol. 222, pp. 581-597.

Nannapaneni, et al., Unstable Expression and Thermal Instability of a Species-Specific Cell Surface Epitope Associated with a 66-Kilodalton Antigen Recognized by Monoclonal Antibody EM-7G1 within Serotypes of Listeria Monocytogenes Grown in Nonselective and Selective Broths, Applied and Environmental Microbiology, dated August 1998, vol. 64, No. 8, pp. 3070-3074.

Nastishin, Brine-Rich Corner of the Phase Diagram of the Ternary System Cetylpyridinium Chloride-Hexanol-Brine, Langmuir dated 1996, vol, 12, pp. 5001-5015.

Pottiez et al., Easily tuneable nonlinear optical loop mirror including low-birefringence, highly twisted fibre with invariant output polarisation, Optics Communication, dated 2004, vol. 229., pp. 147-159.

Poulin, et al., "Novel Collodial Interactions in Anisotropic Fluids", Science, dated 1997, vol. 275, pp. 1770-1773.

Reinders, et al., "Comparison of the Sensitivity of Manual and Automated Immunomagnetic Separation Methods for Detection of Shiga Toxin-Producing *Escherichia coli* O157:H7 in Milk", Journal of Applied Microbiology, dated 2002, vol. 92, pp. 1015-1020.

Sana, et al., "Directed Selection of Recombinant Human Monoclonal Antibodies to Herpes Simples Virus Glycoproteins from Phage Display Libraries", Proc. Natl. Acad. Sci. USA, dated 1995, vol. 92, pp. 6439-6443.

Schneider et al., Self-Assembled Monolayers and Multilayered Stacks of Lyotropic Chromonic Liquid Crystalline Dyes with In-Plane Orientational Order, Langmuir, dated 2000, vol. 16, pp. 5227-5230.

Seabrook, et al., "Modified Antibodies", dated 1991, Stockton Press, pp. 53-77.

Sergan, et al., "Polarizing-Alignment Layers for Twisted Nematic Cells", Liquid Crystals, dated 2000, vol. 27, No. 5, pp. 567-572.

Sevier, et al., "Monoclonal Antibodies in Clinical Immunology", Clinical Chemistry (1981), vol. 27, No. 11, pp. 1797-1805.

Shinagawa, et al., "Immunoreactivity of a Synthetic Pentadecapeptide Corresponding to the N-Terminal Region of the Scrapie Prion Protein", J. Gen. Virol, dated 1986, vol. 67, pp. 1745-1750.

* cited by examiner

DEVICE IMPROVING THE DETECTION OF A LIGAND

BACKGROUND

Early detection of threat agents can be a great benefit in either disease prophylaxis or therapy before symptoms appear or worsen. Every species, strain or toxin of a microbe contains unique surface ligands. Using molecular engineering and/or immunological techniques, receptor molecules, such as antibodies or aptimers, can be isolated that will bind to these ligands with high specificity. Examples of ligand/receptor detection systems for identifying threat agents include, but are not limited to, detection of a pathogenic agent such as a microbe by an antibody, or of a toxin by an antibody, or detection of an antibody in blood by another antibody, or binding of a chemical toxin, such as nerve gas, to its receptor.

Figure 8A:
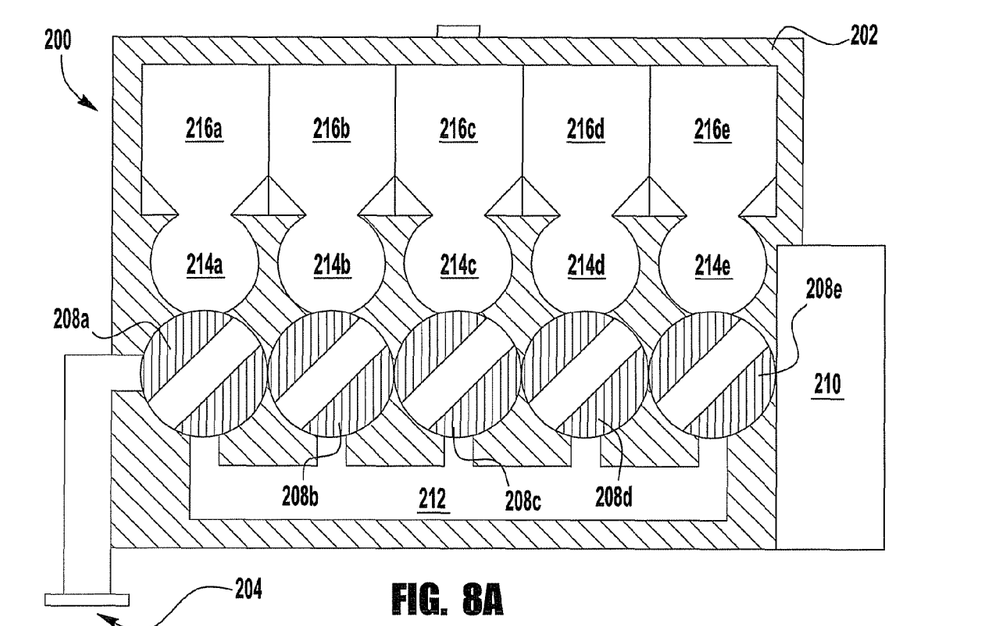
FIG. 8A is a schematic representation of a third embodiment of a device for detecting the presence of a ligand in a sample as disclosed in the present application, shown in a storage orientation.
Figure 8B:
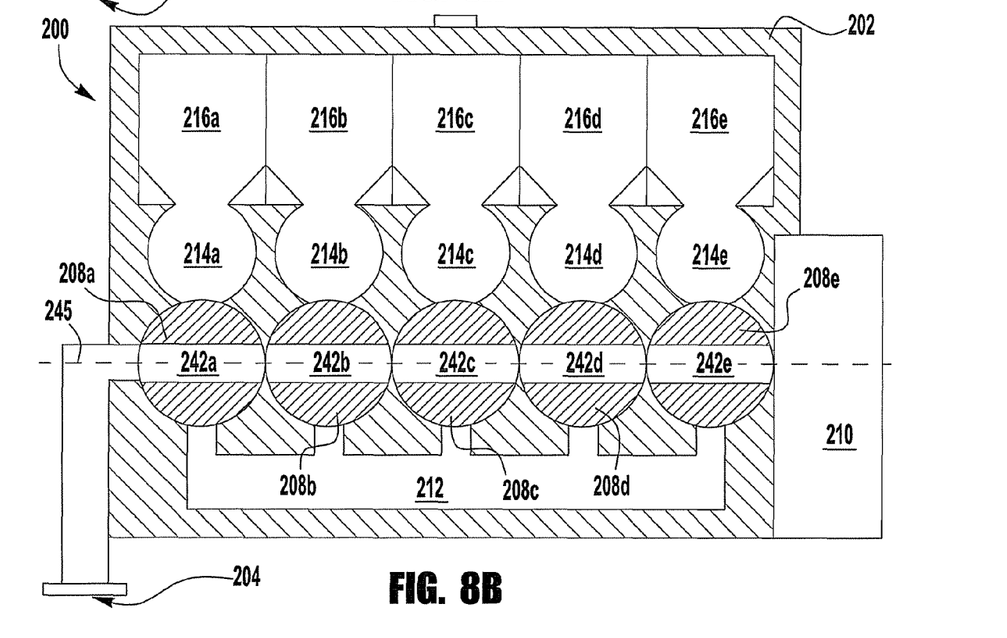
FIG. 8B is a schematic representation of the device of FIG. 8A, shown in a purify/concentrate orientation.
Figure 8C:
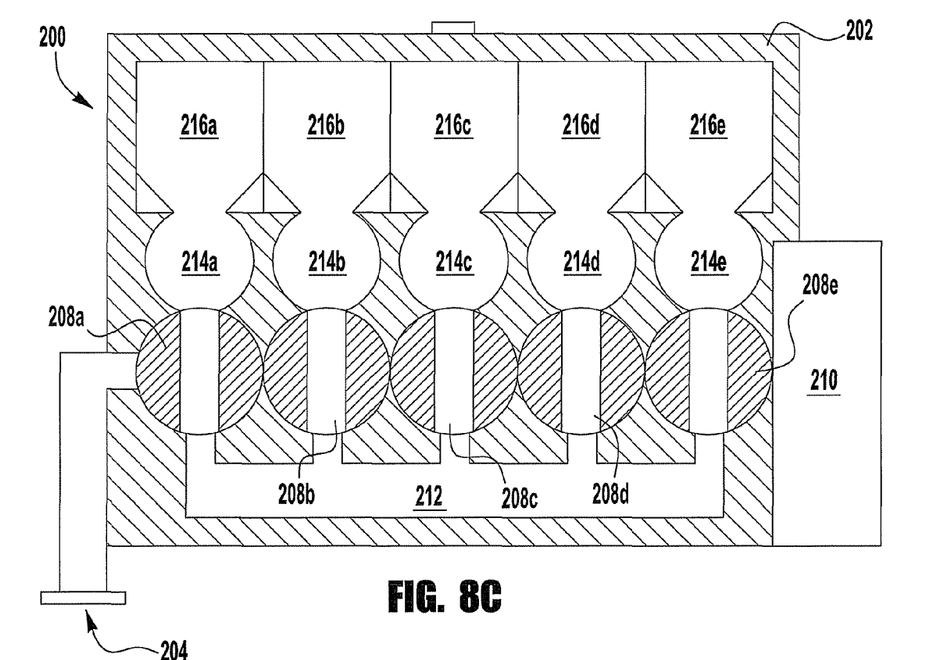
FIG. 8C is a schematic representation of the device of FIG. 8A, shown in a delivery orientation.

U.S. Pat. No. 6,171,802 (the '802 Patent) by Woolverton, Niehaus, Doane, Lavrentovich, Schmidt and Signs, the entire disclosure of which is fully incorporated herein by reference, discloses a system for detecting selective binding of a ligand to a receptor and producing an amplified optical signal as the formed receptor-ligand aggregate distorts the orientation of a surrounding liquid crystal matrix. The system comprises a receptor (e.g., mono-specific antibody), a ligand (e.g., the specific pathogenic agent that binds to the antibody), and a liquid crystalline material. Under baseline conditions, a uniform nematic liquid crystal slab is positioned between two glass plates whose surfaces are treated to uniformly align the liquid crystal (FIG. 8). The resulting cassette is viewed between two polarizers, a director and an analyzer, with the analyzer oriented 90° out of phase with the director. The easy axis orientation of the liquid crystal matrix (i.e., the direction of positional orientation of the liquid crystal) is aligned with the director and light is projected through the device. Since the analyzer is perpendicular to the polarization of light, light is not transmitted across the uniformly aligned detection system and the cassette appears dark. Under assay conditions, however, the receptor-ligand aggregates, also referred to as inclusion bodies, become embedded in the liquid crystal matrix and induct director distortions in that matrix. The magnitude of director distortion is determined by the balance of the liquid crystal-to-particle anchoring energy versus the elastic energy of director distortions in the liquid crystal bulk. Both anchoring energy and elastic energy are affected by particle size such that individual ligands or receptors are too small to induce detectable distortions, i.e., particle diameter (d) is less than the critical detectable diameter ($d_c$). Larger particles, ligand aggregates for example, that exceed the critical diameter will cause the adjacent liquid crystal to deviate from it's original uniform orientation. The distorted zone will permit light transmission and will appear as an optically detectable bright spot.

U.S. Patent Application Publication No. 2002/0052002 by Niehaus, Woolverton, Lavrentovich, Ishikawa and Doane, the entire disclosure of which is fully incorporated herein by reference, discloses an additional system and methods for amplifying receptor-ligand binding to enhance detection signals created in the liquid crystal. The system and method comprise a generally spherical particle capable of binding to the desired ligand. The diameter of the individual spherical particle is less than the critical diameter ($d_c$) and thus does not initiate a detectable optical signal. In one embodiment, the generally spherical particle is coated with a receptor that specifically binds to the ligand (e.g. a microsphere coated with an antibody specific for the ligand). In another embodiment, the system comprises an antibody specific for the ligand, such antibody not being attached to the generally spherical particle. In this latter embodiment, a generally spherical particle is also provided that is coated with a receptor for the antibody (e.g., a microsphere coated with anti-immunoglobulin). The system also comprises a liquid crystalline material. In the absence of a ligand to which the antibody binds, the liquid crystalline material assumes an ordered orientation, and polarized light directed through the system, similar to the description above, does not reach a light detector. In the presence of a ligand to which the antibody can bind, however, the microsphere-antibody-ligand complex becomes large enough to exceed the critical diameter, distorts the liquid crystalline material, and allows local transmission of light to the photodetector. The generally spherical particle thus significantly enhances formation of detectable ($d \gg d_c$) microsphere-antibody-ligand aggregates when ligand concentrations are low.

U.S. Pat. No. 7,060,225 (the '225 Patent) by Niehaus, the entire disclosure of which is fully incorporated herein by reference, discloses a self-contained device, called an assay cassette, for rapid, safe, and automatic detection of biohazardous ligands. The cassette comprises one or more mixing chambers configured for mixing various assay components with an introduced sample, such assay components being a receptor (e.g., an antibody) capable of binding to the ligand, an optional generally spherical particle capable of binding to the receptor (e.g., microspheres coated with antibody); and a liquid crystalline material. The device is configured to provide for turbulent flow of the sample and assay components such that there is mixing between the sample and assay components. The device also comprises detection chambers into which the sample that has been mixed with the assay components (i.e., mixed sample) flows. The device is also configured to provide for laminar flow of the mixed sample into the detection chambers such that the liquid crystalline material assumes a uniform alignment with the director except when adjacent to an inclusion body whose diameter exceeds the critical diameter ($d \gg d_c$), e.g., surrounding immune aggregates. The local liquid crystal distortions allow transmission of spots of polarized light through the detection chamber for identification by a photodetector.

SUMMARY

The present application generally discloses a device and method for improving the detection of a ligand by a receptor. More specifically, the present application discloses a device capable of concentrating microbes by removing particulates from fluid-borne samples, and/or causing selective aggregation of concentrated microbes.

In an illustrated embodiment of a device applying at least some of the principles of the invention, a device is provided that acts as a multipath valve capable of changing between a storage orientation, a purifying/concentrating orientation, and a delivery orientation. In one embodiment, a device is disclosed having a body that defines an inlet, a first outlet, a second outlet, and a mixing chamber. The body further supports a pathogen capture unit that defines a passage or throughbore adapted to house a receptor that exhibits specificity for a ligand. The capture unit being movable between a first orientation in which the inlet is in fluid communication with the first outlet via the passage, and a second orientation in which the passage is in fluid communication with the mixing chamber. In another embodiment, the capture unit houses a plurality of antibody coated generally spherical particles capable of binding to a ligand.

There are numerous embodiments of the methods and devices described herein, all of which are intended to be non-limiting examples. Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

BRIEF DESCRIPTION OF THE DRAWINGS

In the accompanying drawings, which are incorporated in and constitute a part of the specification, embodiments of the invention are illustrated, which, together with the detailed description given below, serve to exemplify embodiments of the invention:

FIG. 7A-7C is a schematic representation of an embodiment of an actuating assembly for changing the orientation of the device of FIGS. 4A-4C;

DETAILED DESCRIPTION

While various aspects and concepts of the invention are described and illustrated herein as embodied in combination in the embodiments, these various aspects and concepts may be realized in many alternative embodiments, either individually or in various combinations and sub-combinations thereof. Unless expressly excluded herein all such combinations and sub-combinations are intended to be within the scope of the present invention. Still further, while various alternative embodiments as to the various aspects and features of the invention, such as alternative materials, structures, configurations, methods, devices, and so on may be described herein, such descriptions are not intended to be a complete or exhaustive list of available alternative embodiments, whether presently known or identified herein as conventional or standard or later developed. Those skilled in the art may readily adopt one or more of the aspects, concepts or features of the invention into additional embodiments within the scope of the present invention even if such embodiments are not expressly disclosed herein. Additionally, even though some features, concepts or aspects of the invention may be described herein as being a preferred arrangement or method, such description is not intended to suggest that such feature is required or necessary unless expressly so stated. Still further, or representative values and ranges may be included to assist in understanding the present invention however, such values and ranges are not to be construed in a limiting sense and are intended to be critical values or ranges only if so expressly stated. The embodiments described in the summary and throughout the specification are not intended to limit the meaning or scope of the claims in any way. The terms used in the claims have all of their full ordinary meaning.

It should be noted that for the purposes of this application, the terms attach (attached), connect (connected), and link (linked) are not limited to direct attachment, connection, or linking but also include indirect attachment, connection, or linking with intermediate parts, components, or assemblies being located between the two parts being attached, connected, or linked to one another. In addition, the terms attach (attached), connect (connected), and link (linked) may include two parts integrally formed or unitarily constructed.

Figure 1A:
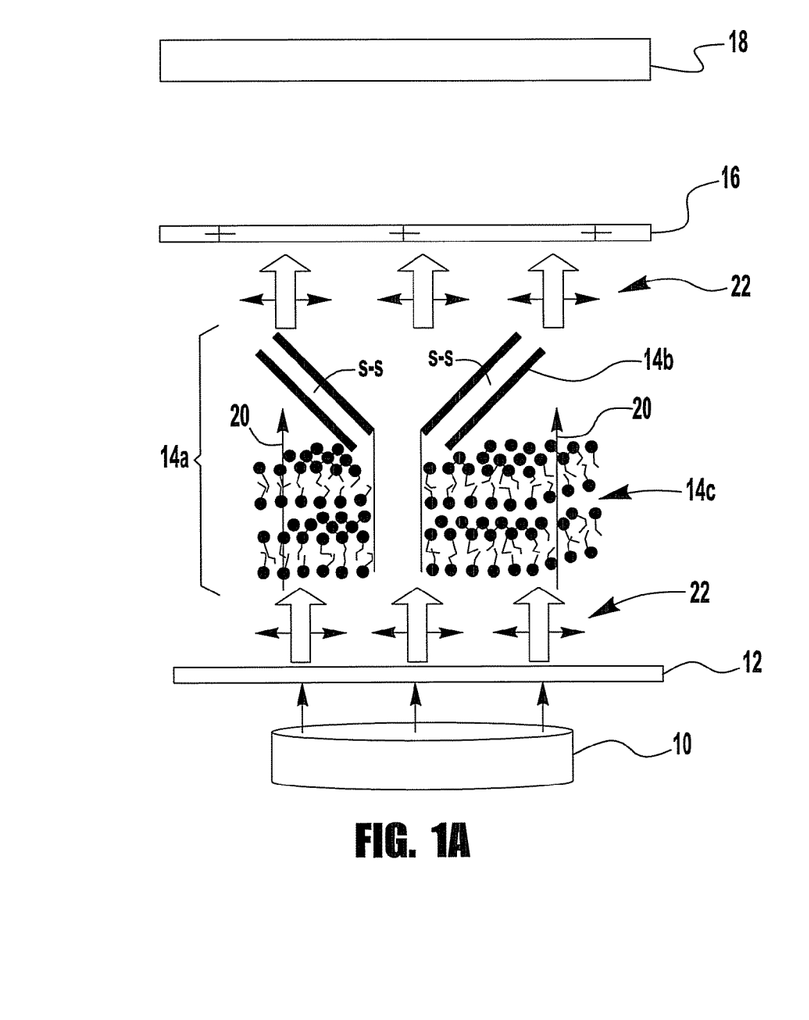
FIG. 1A is a schematic representation of an amplification mechanism with a receptor inserted in the lyotropic liquid crystal. See U.S. Pat. No. 6,171,802.
Figure 1B:
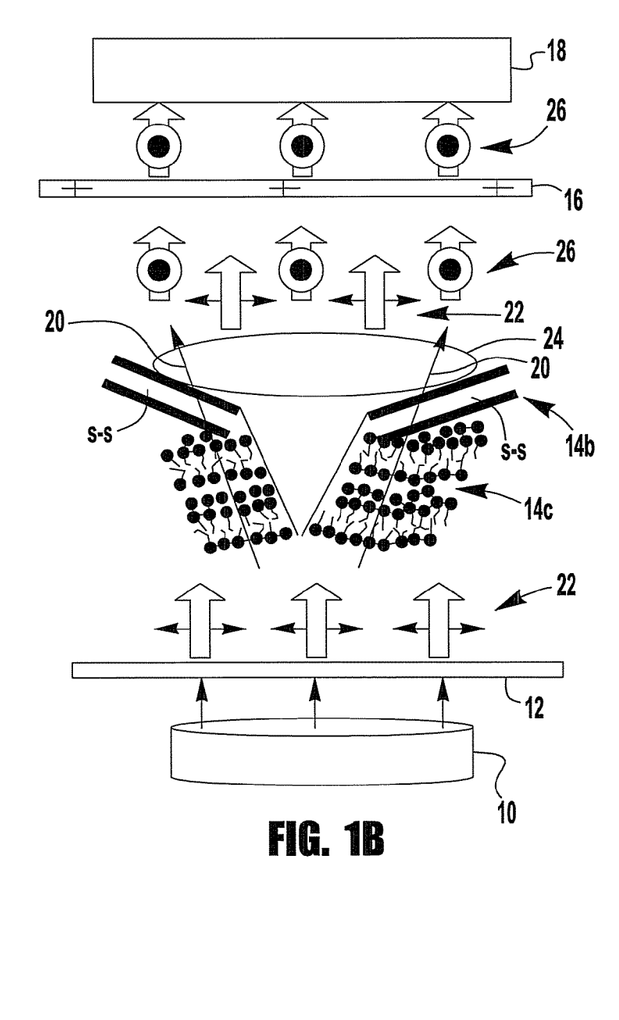
FIG. 1B is a schematic representation of an amplification mechanism with the specific ligand bound to its receptor causing deformation of the liquid crystal and alteration of the transmission of polarized light. See U.S. Pat. No. 6,171,802.

FIGS. 1A and 1B illustrate a method disclosed in U.S. Pat. No. 6,171,802 for detecting selective binding of a ligand to a receptor and producing an amplified optical signal as the formed receptor-ligand aggregate distorts the orientation of a surrounding liquid crystal matrix. As shown in FIGS. 1A and 1B, the device consists of a light source 10, an initial polarizer 12, with the direction of polarization in the plane of the figure, a pathogen detection system 14a, comprising antibodies 14b embedded in biphilic, lyotropic liquid crystalline material 14c, a secondary polarizer 16, with the direction of polarization perpendicular to the plane of the figure, and a photodetector 18.

In operation, the initial polarizer 12 organizes a light stream 22 that is linearly polarized in the plane of the figure. The optical axis 20 of the inactivated device is perpendicular to the pathogen detection system 14a, and thus no birefringence of the transluminating linearly polarized light stream 22 occurs. Since the polarization direction of the secondary polarizer 16 is perpendicular to the transluminating linearly polarized light 22, the secondary polarizer prevents light from reaching the photodetector 18.

Binding of a ligand 24, such as a microbe, to the receptor 14b, such as an antibody, distorts the liquid crystal 14c, induces birefringence and thus causes the generation of detectable light. The receptor (antibody) 14b is embedded in the biphilic, lyotropic liquid crystal 14c. The spacial distortion caused by the formation of the antigen-antibody complex is transmitted to the contiguous liquid crystal 14c. The elastic characteristics of the liquid crystal permit the distortion to be transmitted over a region much larger than the size of the receptor-ligand complex. This allows the use of the standard optical phenomenon of birefringence to detect distortions caused by the receptor-ligand complex. The altered liquid crystalline order tilts the optical axis 20 and induces birefringence. In other words, the incident polarized light 22 gives rise to two refracted light waves: the ordinary wave and the extraordinary wave with the mutually orthogonal polarizations (see, Max Born and E. Wolf, Principals of Optics, Sixth edition, Pergaman Press, Oxford, 1980), incorporated herein by reference. Thus, there is a portion of light 26 in which the optic vibrates in the direction of the secondary polarizer 16. The secondary polarizer (analyzer) 16 allows this portion of the light to pass to the photodetector 18. The detected change or amplification in light intensity can be transduced electronically into a perceptible signal.

Figure 2:
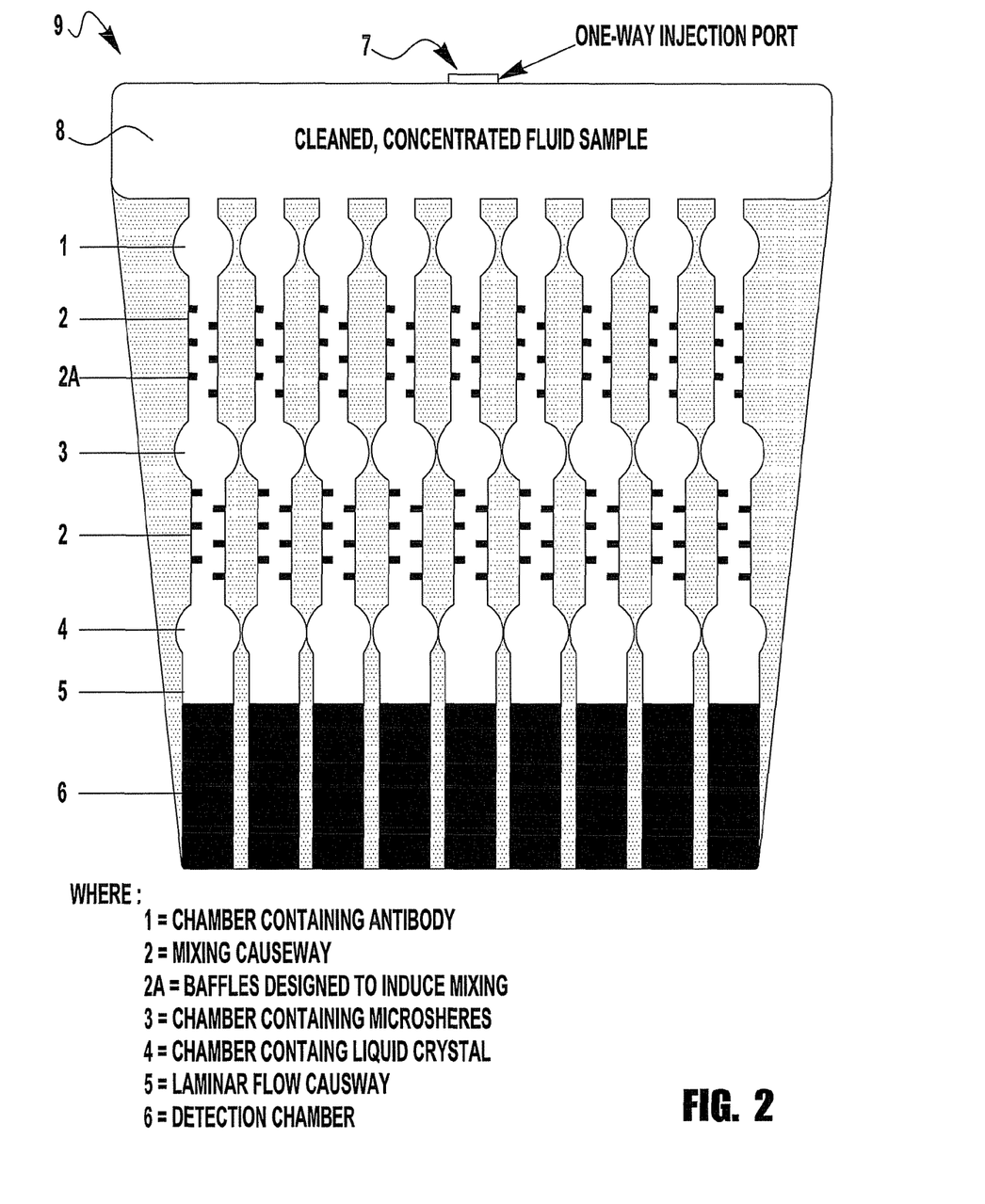
FIG. 2 is a schematic representation of a self-contained assay cassette for use in detecting the presence of a ligand in a sample. See U.S. Pat. No. 7,060,225.

FIG. 2 illustrates an embodiment of a self-contained, multiwell assay cassette disclosed in the '225 Patent. The cassette 9 is generally a linear flow system adapted to mix a fluid sample with the various assay components. In the depicted embodiment, the cassette 9 includes a one-way injection port 7 leading to a first chamber 8 that is connected to a plurality sampling flow paths. Each flow path includes, in sequential order, a chamber containing an antibody 1, a first mixing causeway 2 containing baffles 2a designed to induce mixing, a chamber containing generally spherical particles 3, a second mixing causeway 2, a chamber containing a liquid crystal material 4, a laminar flow causeway 5, and a detection chamber 6.

A sample introduced into the injection port 7 flows through the cassette and is sequentially mixed with the receptors (e.g., antibodies that specifically bind to the ligand in the sample), generally spherical particles (e.g., microspheres) coated with or capable of binding to the antibodies, and the liquid crystalline materials. The mixing occurs through turbulent flow of the sample and assay components, which flow is provided by the embodiment of the cassette. After the addition and mixing of the assay components with the sample, the design of the assay cassette provides for laminar flow of the mixed sample into the detection chambers 6. In the presence of ligand/receptor complex aggregates, the orientational order of the liquid crystalline material surrounding the complex is distorted, as described above with respect to the '802 Patent, and allows polarized light to be transmitted through the detection chamber. In the absence of a complex between a ligand and a receptor, the orientational order of the liquid crystalline material is not distorted, and polarized light is not transmitted through the detection chamber.

Figure 3:
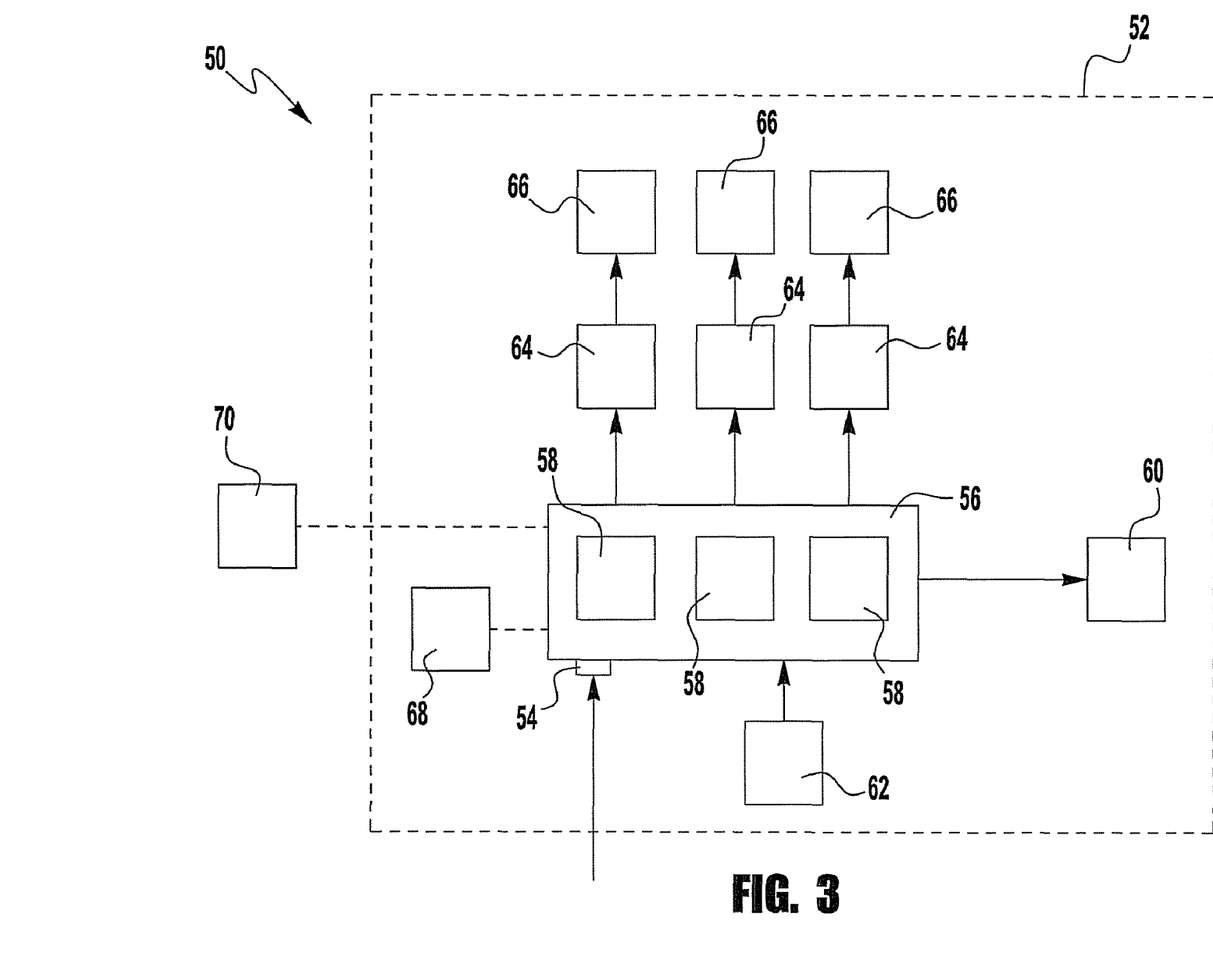
FIG. 3 is a schematic representation of a first embodiment of a device for detecting the presence of a ligand in a sample as disclosed in the present application.

FIG. 3 illustrates a schematic representation of an embodiment of a device 50 for improving the detection of the presence of a ligand in a sample. The device 50 includes a body 52 defining an inlet port 54. The body 52 may, for example, define or be a portion of an assay cassette. The device 50 includes a purifying/concentrating device 56 having one or more pathogen capture units 58. In the depicted embodiment, three pathogen capture units 58 are illustrated, though other embodiments of the device may include more or less than three. The purifying/concentrating device 56 is adapted to purify selected microbes by retaining the microbes in selected capture units 58 and adapted to concrete the sample by diverting excess volume and non-specific particulates from the capture units. Each pathogen capture unit 58 may house a receptor that exhibits specificity for a ligand. A different receptor may be housed in each capture unit 58. Furthermore, each pathogen capture unit 58 may house a plurality of generally spherical particles (not shown), such as for example, microspheres, that are coated with and/or exhibit specificity to the receptor. The device 50 is configured such that the purifying and concentrating device 56 is the first portion of the device coming in contact with an infused sample.

The device 50 may be configured to switch between two or more orientations. For example, in a first orientation, the device 50 may be configured to define a flow path that allows an injected sample to flow through the one or more capture units 58, and into a first reservoir 60. As the sample flows through the one or more capture units 58, the ligand in the sample is exposed to the receptors in the capture units. If a capture unit contains a receptor that exhibits specificity to the particular ligand in the sample, the ligand will bind to the receptor to form a ligand-receptor aggregate. The excess fluid and particulates that flow through the capture units 58 collect in the first reservoir 60. A flushing or buffer solution may also be injected into the device via the inlet port 54 to wash any non-adherent particles from the pathogen capture units 58 into the first reservoir 60. The first reservoir 60 may be integrally formed with the body, but other arrangements in which the first reservoir is not integrally formed with the body are possible.

In a second orientation, the device 50 may be configured to allow a buffer solution for a fluid source to flow through each of the pathogen capture units 58, and into mixing chambers 64 and detection chambers 66 associated with each of the capture units 58. For example, the device 50 may include a second reservoir 62 that contains the buffer solution. The second reservoir 62 may be integrally formed with the body, but other arrangements in which the second reservoir is not integrally formed with the body are possible. The mixing chamber(s) 64 (containing a liquid crystal material) and the detection chamber(s) may be configured, for example, as disclosed in the '225 Patent.

The device 50 may also include a means for changing the orientation of the device 68. For example, the device 50 may include a mechanical actuating assembly 68 for moving one or more components, such as for example, changing the orientation of the pathogen capture units 58, in order to change the device orientation. The device 50 may also include a means for selectively retaining the receptor 70 within the pathogen capture unit. For example, in one embodiment, the generally spherical particles may be magnetic and a source of a magnetic field, such as an electromagnet, for example, may be used to selectively anchor the magnetic spherical particles (and receptor) within the pathogen capture units. In another embodiment, the means for selectively retaining the receptor 70 within the pathogen capture unit may include a screen, filter, sieve or other structure that allows a fluid sample to flow past or through the structure but prevents the receptor from flowing past or through the structure. For example, a screen having a mesh size sufficient to block the generally spherical particles may be used.

In a third orientation, the device 50 may be configured to seal the pathogen capture units 58 for storage. For example, the mechanical actuating assembly 68 may change orientation of the pathogen capture units 58 such that the flow path through the capture units is sealed or blocked.

Figure 4A:
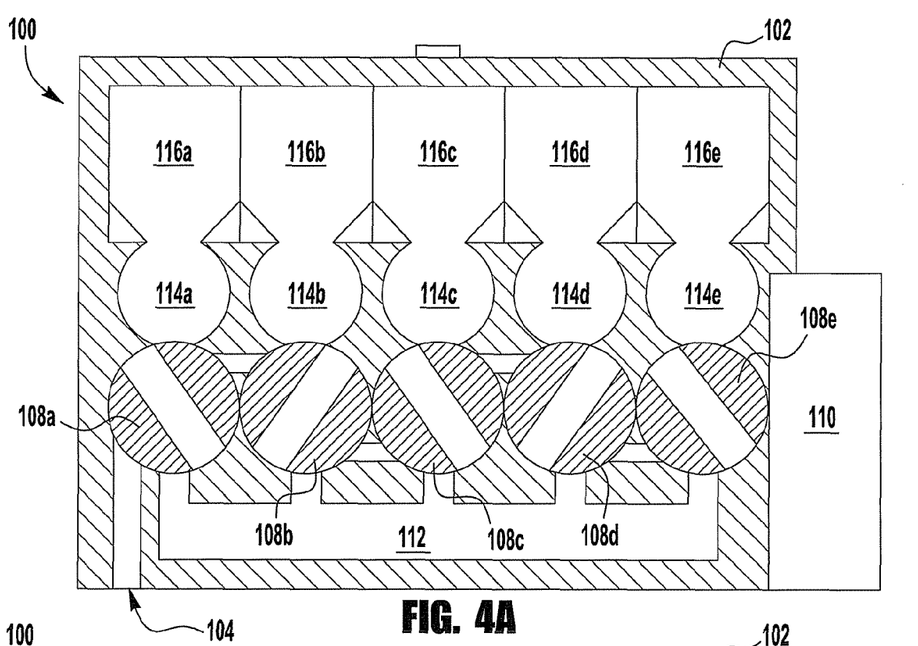
FIG. 4A is a schematic representation of a second embodiment of a device for detecting the presence of a ligand in a sample as disclosed in the present application, shown in a storage orientation.
Figure 4B:
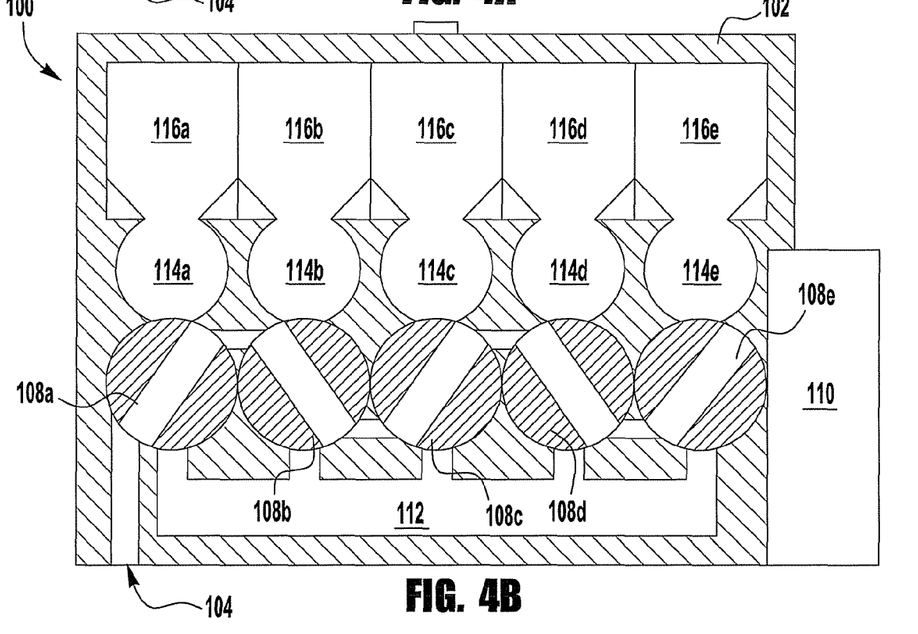
FIG. 4B is a schematic representation of the device of FIG. 4A, shown in a purify/concentrate orientation.
Figure 4C:
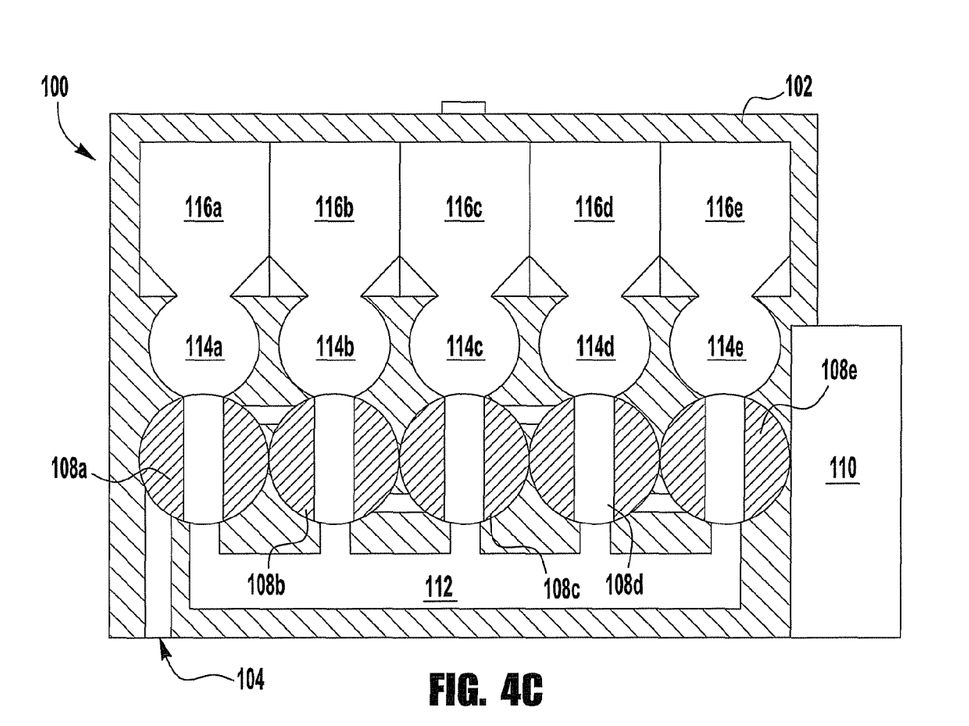
FIG. 4C is a schematic representation of the device of FIG. 4A, shown in a delivery orientation.

Referring to FIGS. 4A-4C, a second embodiment of a device 100 for improving the detection of the presence of a ligand in a sample is illustrated. In the depicted embodiment, the device 100 includes a body 102, an inlet port 104, one or more pathogen capture units 108a-e, a first reservoir 110, a second reservoir 112, one or more mixing chambers 114a-e, one or more detection chambers 116a-e, a means for changing the orientation of the capture units 108a-e (see FIGS. 7A-7C), and a means for selectively retaining the one or more receptors within the capture units (FIG. 5).

Figure 5:
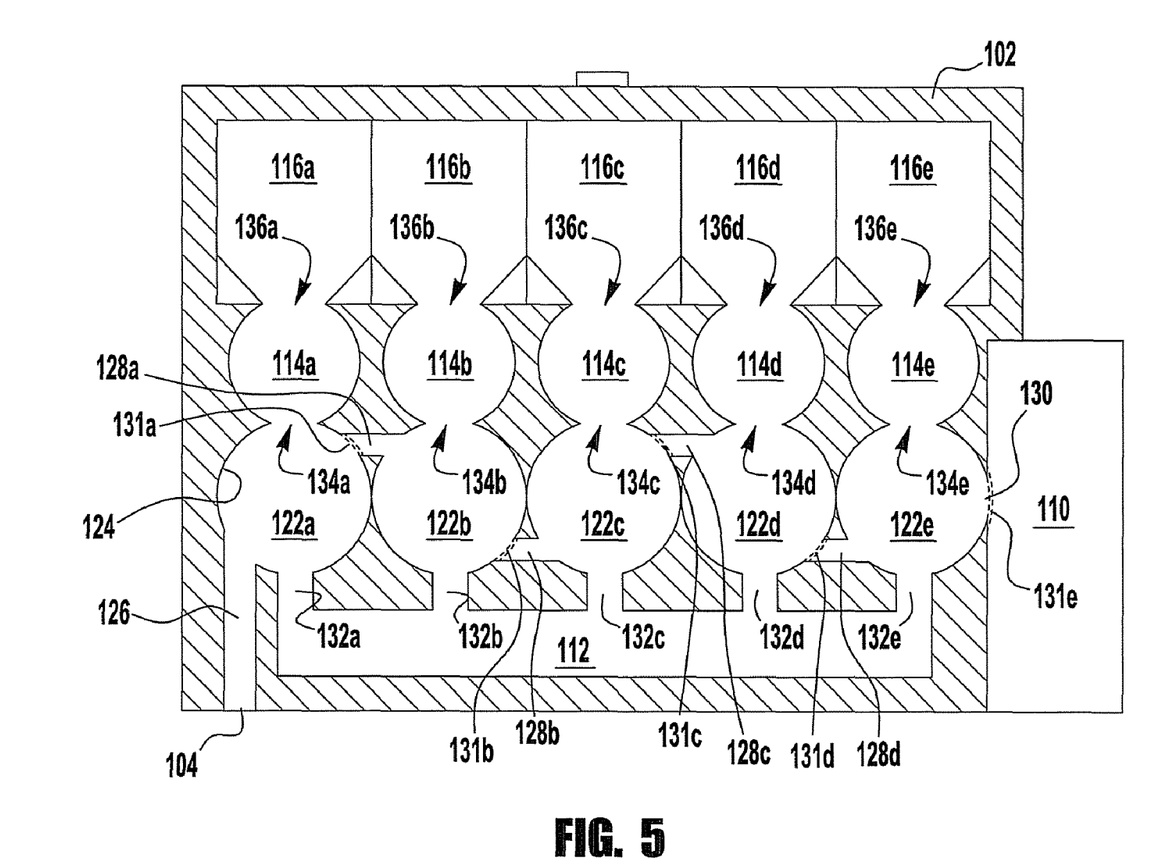
FIG. 5 is a schematic representation of an embodiment of a body of the device of FIG. 4A.

Referring to FIG. 5, the body 102 may be configured in a variety of ways. Any structure capable of facilitating the capture of and detection of a ligand in a sample may be used. In the depicted embodiment, the body 102 is realized as a self-contained, multi-well assay cassette that defines and interconnects a plurality of chambers and reservoirs via flow passages or openings. For example, the body 102 defines one or more chambers 122 adapted to receive the one or more capture units 108a-e. In the depicted embodiment, the capture units 108a-e are realized as generally circular disks, thus the chambers 112 are defined by a generally spherical wall 124 adapted to generally conform to the shape of the capture units. The depicted embodiment includes five capture unit chambers 122a-e and five capture units 108a-e (FIGS. 4A-4C). Other embodiments of the device, however, may have more or less than five chambers and units.

The inlet port 104 is in fluid communication with the first capture unit chamber 122a via the first flow path 126. Each subsequent fluid capture unit chamber 122b-122e is in fluid communication with the previous capture unit chamber 122a-d, respectively, by a respective interconnecting flow passage 128a-d. The fifth capture unit chamber 122e is in fluid communication with the first reservoir 110 via a second flow passage or opening 130. Thus, a flow path is formed from the inlet 104, through the capture unit chambers 122a-e in series, and into the first reservoir 110.

In the depicted embodiment, a filtering structure, such as but not limited to a screen, filter, or sieve, 131a-e, is disposed in each of the interconnecting flow passages 128a-d and the second flow passage or opening 130 to act as a means for selectively retaining the receptors in the capture units 108a-e during a purify/concentrate phase, as described in more detail below. The filtering structures 131a-e are configured to allow a fluid sample to flow through but block the generally spherical particles from exiting the capture units along with the fluid sample.

Each capture unit chamber 122a-e, is also in fluid communication with the second reservoir 112 via a respective flow passage 132a-e. Thus, each of the capture unit chambers 122a-e are connected to the second reservoir 112 in parallel. Likewise, each capture unit chamber 122a-e is connected to a respective mixing chamber 114a-e via a respective flow passage or opening 134a-e and each mixing chamber 114a-e is connected to a respective detecting chamber 116a-e via a respective flow passage or opening 136a-e. Thus, each capture unit chamber 122a-e has a respective mixing chamber 114a-e and a respective detecting chamber 116a-e associated with it.

In the depicted embodiment, therefore, each capture unit chamber 122a-e has two inlets and two outlets associated with it. For example, the first capture unit 122a has a first inlet defined by the fluid passage 126, a second inlet defined by the flow passage 132a, a first outlet defined by the interconnecting passage 128a to the second capture unit chamber 122b, and a second outlet defined by the flow passage or opening 134a to the first mixing chamber 114a.

The body 102 may be formed in a variety of ways and made from any suitable material, such as, but not limited to, plastic or glass. In one embodiment, the body 102 has an upper layer and a lower layer. The upper layer may include a hard plastic, such as polystryrene and the lower layer may include a softer type of plastic, such as polypropylene, or another type of collapsible plastic (e.g. blister pack material). The lower layer may be attached to the upper layer is such a way as to form discrete walls and chambers. The detection chambers 116a-e may include at least two opposing sides of low or non-birefringent glass. In one embodiment, the device is in the size range of about 1 to about 6 inches long, about 0.5 to about 6 inches wide and about 0.01 to about 1 inch thick.

Referring to FIG. 4A, each capture unit 108a-e is received within each of the capture unit chambers 122a-e in the body 102. In the depicted embodiment, five capture units 108a-e are illustrated. Other embodiments, however, may include more or less than five capture units.

Figure 6:
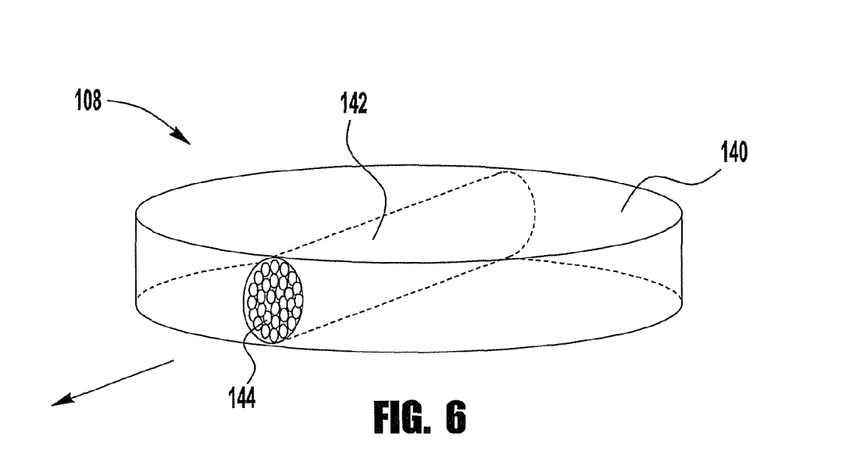
FIG. 6 is a perspective view of a first embodiment of a capture unit for use with the device of FIGS. 4A-4C.

FIG. 6 illustrates an embodiment of a capture unit 108. The capture unit(s) 108 may be configured in a variety of ways. Any structure capable of housing a receptor, and optionally a generally spherical particle coated with a receptor or capable of binding to a receptor, such that a ligand in an infused sample may bind with the receptor and be transferred along the detection flow path may be used. In the depicted embodiment, the capture unit 108 has a generally disk-shaped body 140 defining a generally cylindrical passage or through bore 142 that transects the diameter of the capture unit. The passage 142, however, may be configured in a shape other than cylindrical.

The capture unit 108 may be made of a variety of materials, such as but not limited to a plastic material. In the depicted embodiment, an optional set of generally parallel tubes 144 are longitudinally disposed in the cylindrical passage 142 to increase the surface area that can come in contact with a perfusing sample. Each tube 144 extends the length of the cylindrical passage 142 and defines a bore or passage through each tube. The tubes 144 may be made of a variety of material, such as but not limited to, a thin plastic material. In other embodiments, the parallel passages may be formed by one or more structures other than tubes and may be shaped other than cylindrical. For example, a single honeycomb structure may be disposed in the passage 142 to form a set of generally parallel flow paths.

One or more generally spherical particle(s) capable of binding to a ligand are provided in each capture unit. For example, each tube 144 in each capture unit 108 may contain one or more generally spherical particles. In one embodiment, the generally spherical particle is coated with a receptor that specifically binds to the ligand (e.g. a microsphere coated with an antibody specific for the ligand). In another embodiment, an antibody specific for the ligand is provided, but that antibody is not coated or attached to the generally spherical particle. The generally spherical particle, instead, is coated with a receptor for the antibody (e.g., a microsphere coated with anti-immunoglobulin) (see U.S. Patent Application Publication No. 2002/0052002). The generally spherical particles may be configured in a variety ways, such as different materials, different sizes, and various number of particles in each capture unit. In one embodiment, polystyrene balls, each having a diameter of approximately 1-3 microns are used.

Referring to FIGS. 4A-4C, each capture unit 108 is movable within a respective capture unit chamber 122a-e in the body 102. For example, in the depicted embodiment, each capture unit 108a-e is rotatably disposed within the body 102. The capture unit/body assembly is designed to function as a multi-path valve. Changing the orientation of the capture units 108 relative to the body 102, places various chamber, ports, and reservoirs in fluid communication with each other.

Figure 7A:
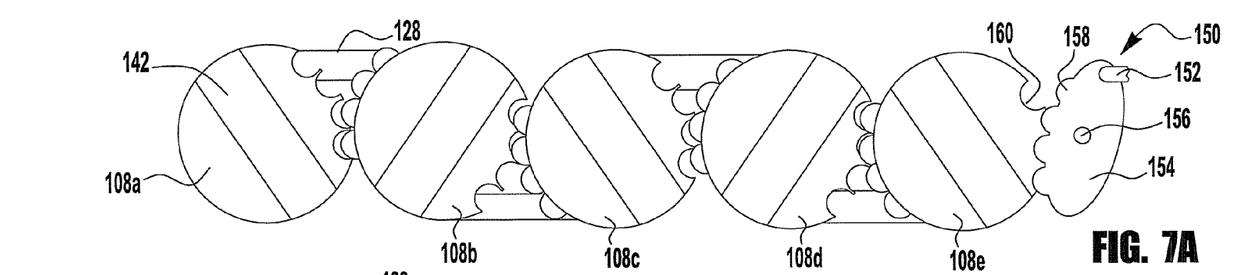

Referring to FIGS. 7A-7C, the capture units 108a-e are linked and movable by an actuating assembly 150 capable of rotating the disks within their capture unit chambers 122a-e to change the configuration of the device 100. The actuating assembly 150 may be configured in a variety of ways. Any structure, assembly or apparatus capable of changing the orientation of the capture units to change the configuration of the device 100 may be used. In the depicted embodiment, the actuating assembly 150 includes an actuating arm 152 and a rotatable cam 154. The cam 154 is rotatable about a pivot point 156 and includes a set of gear teeth 158 adapted to mate with a corresponding set of gear teeth 160 arranged on the perimeter of an adjacent capture unit 108e. Each adjacent capture unit 108a-d includes a corresponding set of gear teeth 160 adapted to mate with a corresponding set of gear teeth on an adjacent capture unit. Movement of the actuating arm 152 results in rotation or pivotal movement of the cam 154 about the pivot point 156. The cam 154 transfers the rotational movement through the corresponding gear teeth to rotate each of the capture units 108 at the same time.

FIG. 4A illustrates the device 100 in a storage configuration. In this configuration, each passage or throughbore 142 of each capture unit is blocked or closed by a segment of solid cylindrical 124 of each capture unit chamber 122a-e. Thus, the receptors (and optional generally spherical particles) are trapped within their respective passage.

Figure 7B:
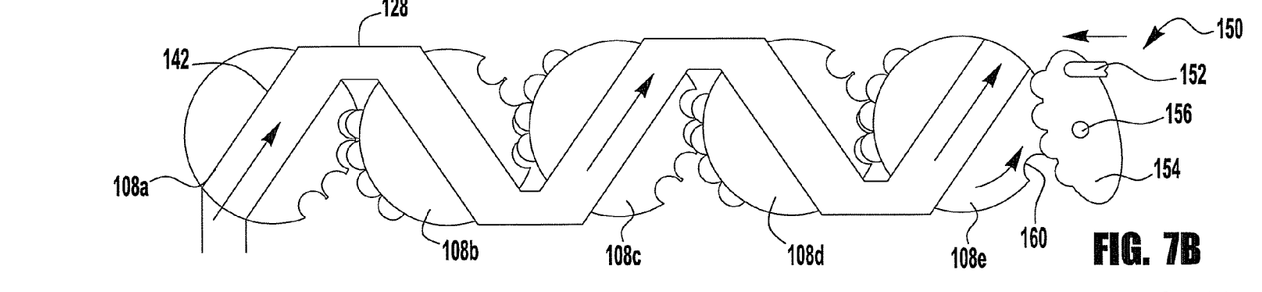

Referring to FIG. 4B, the device is converted to a purify/concentrate configuration by actuating the actuating assembly (FIG. 7B) to rotate the capture units 108a-e to form a continuous perfusion path from the injection port 104, through the capture units 108a-e and interconnecting passages 128a-128d in series, to the first reservoir 110. In addition, a means for selectively retaining the receptors within their respective passages in the capture units may be provided. In the depicted embodiment of FIG. 5, the filtering structures 131a-e block the generally spherical particles from flowing through the interconnecting passages 128a-d and the second flow passage 131, thus retaining the particles in the capture units 108a-e. In another embodiment, which may or may not include filtering structures, magnetic, antibody-coated, generally spherical particles are used to bind to a ligand. To selectively anchor the particles within the capture units, an electromagnet is positioned such that when activated, the particles are held in their respective capture unit.

Thus, an embodiment of a method to purify and concentrate a sample using the device 100 includes, utilizing a means for anchoring one or more receptors in the pathogen capture units and injecting a sample into the inlet port 104. For example, a sample-filled syringe may be attached to a luer port at the inlet 104 (the port may incorporate a course filter to remove large particulates) and depressed to force sample from the syringe along the path, past the anchored magnetic antibody coated particles and into the first reservoir 110. The inlet port 104 may be adapted to include a one-way valve such that once the sample is introduced into the device 100, the sample or its contents do not escape from the device and contact with the operator, for example. In one embodiment, the inlet port is a rubber barrier through which the syringe needle is inserted, and the plunger of the syringe is depressed for the purpose of expelling the sample contained within the syringe into the sample chamber of the assay cassette. Upon removal of the needle from the port, expansion of the rubber to occlude the hole where the needle had been inserted prevents flow of sample out of the cassette. Other designs for one-way ports are possible, and are known in the art.

As the injected sample flows from the inlet 104 to the first reservoir 110, the sample will come in contact with all of the segregated receptors in the respective capture units 108a-e. A specific microbe, however, will only be captured by its selective antibody. The majority of the remaining non-adherent sample particulates and the excess sample volume flow into and accumulate in the first reservoir 110. Thus, the first reservoir 110 acts as a waste reservoir in the depicted embodiment. To further concentrate the sample, a buffer solution can then be injected into the device 100 to flow along the path to flush any remaining non-adherent sample particulates from the capture units 108a-e into the first reservoir 110. In this way, this process selectively purifies and concentrates microbes while clearing non-specific particulates.

Figure 7C:
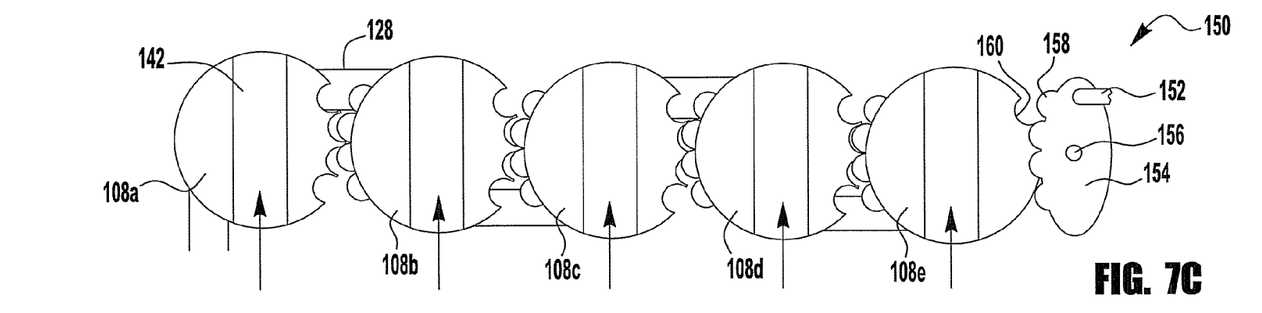

Referring to FIG. 4C, the device 100 is converted to the delivery configuration by actuating the actuator assembly 150 to rotate the capture units 108a-e (FIG. 7C) so that the passage 142 in each of the capture units is arranged to place the second reservoir 112 in fluid communication with the assay path comprising the mixing chambers 114a-e and the detecting chambers 116a-e. Rotation of capture units 108a-e (FIG. 7C) creates a flow path that is unobstructed by screens and thus the ligand-receptor aggregates are delivered to the assay path. Alternatively, magnetic particle-microbe aggregates would be permitted to enter the flow path by deactivation of the electromagnet. Then, flowing a solution, such as a buffer solution, from the second reservoir 112, through the capture units 108a-e, in parallel, and into the respective mixing chambers 114a-e. The mixing chambers 114a-e may be filled with a liquid crystal material such that the ligand-receptor aggregate mixes with the liquid crystal and the sample can be processes as disclosed in the '802 Patent and the '225 Patent.

Referring to FIGS. 8A-8C, a third embodiment of a device 200 for detecting a ligand in a sample is disclosed. The embodiment of the device 200 is similar to the device 100 of FIGS. 4A-4C in that it includes a body 202, an inlet port 204, a first reservoir 210, a second reservoir 212, one or more mixing chambers 214a-e, one or more detection chambers 216a-e and one or more pathogen capture units 208a-e movable disposed in the body, each capture unit having a passage 242 extending through the unit. The body 202 in this embodiment, however, does not include the interconnecting passages 128a-d (FIG. 5) disclosed with the embodiment of the device 100 of FIGS. 4A-4C. Instead, when the device 200 is in the purify/concentrate configuration (FIG. 8B) a generally linear flow path is formed from the injection port 204, through the passages 242a-e of the respective capture units 208a-e, in series, and to the first reservoir 210. For example, the passage 242a of the first pathogen capture unit 208a is generally aligned along an axis 245 with the passage 242b of the second pathogen capture unit 208b such that fluid exiting the first passage 242a enters the adjacent passage 242b and so on for the remaining pathogen capture units.

When transitioning between the storage orientation (FIG. 8A), the purify/concentrate orientation (FIG. 8B) and the delivery orientation (FIG. 8C) of the device 200, the actuating assembly (not shown) moves the pathogen capture units 208a-e in unison between the different orientations.

The invention has been illustrated by the above description of embodiments, and while the embodiments have been described in some detail, it is not the intent of the applicants to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicants' general or inventive concept.

The invention claimed is:

1. A device for detecting the presence of a ligand in a sample, comprising:
   a body defining an inlet, a first outlet, a second outlet, and a mixing chamber;
   a capture unit supported in the body, the capture unit defining a passage housing a receptor that exhibits specificity for a ligand, the capture unit being movable between a first orientation in which the inlet is in fluid communication with the first outlet via the passage, and a second orientation in which the passage is in fluid communication with the mixing chamber; and
   a second capture unit supported in the body, the second capture unit defining a second passage housing a second receptor that exhibits specificity for a ligand, wherein in the first orientation the passage of the capture unit is in fluid communication with the second passage of the second capture unit.

2. The device of claim 1 wherein in the second orientation the passage is in fluid communication with the mixing chamber via the second outlet.

3. The device of claim 1 further comprising a first reservoir in fluid communication with the first outlet.

4. The device of claim 1 further comprising a second reservoir, wherein in the second orientation, the second reservoir is in fluid communication with the second outlet via the passage.

5. The device of claim 1 wherein the mixing chamber contains a liquid crystal material.

6. The device of claim 1 further comprising a plurality of generally spherical particles disposed in the passage, each generally spherical particle is coated with the receptor.

7. The device of claim 1 further comprising a plurality of generally spherical particles disposed in the passage, each generally spherical particle exhibits specificity to the receptor.

8. The device of claim 6 wherein the plurality of generally spherical particles are magnetic.

9. The device of claim 8 further comprising an electromagnet positioned to retain the generally spherical particles within the passage when the electromagnet is activated.

10. The device of claim 6 further comprising one or more structures defining a plurality of parallel flow paths extending the length of the passage, wherein the plurality of generally spherical particles are disposed in the plurality of parallel flow paths.

11. The device of claim 6 further comprising one or more filtering structures adapted to retain the generally spherical particles within the passage in the first orientation.

12. The device of claim 1 wherein the passage has an inlet and an outlet, and wherein the capture unit is movable to a third orientation in which the inlet and the outlet are blocked.

13. The device of claim 1 further comprising a linking assembly adapted to move the capture unit between the first orientation and the second orientation.

14. The device of claim 13 wherein the capture unit comprising a first set of gear teeth and the linking assembly comprises a second set of gear teeth adapted to mate the first set of gear teeth.

15. The device of claim 14 wherein the first set of gear teeth are arranged on the perimeter of the capture unit and the second set of gear teeth are arranged on a movable actuating member, wherein movement of the actuating member rotates the capture unit between the first orientation and the second orientation.

16. The device of claim 1 comprising a plurality of capture units disposed in the body.

17. An assay cassette for detecting the presence of a ligand in a sample, comprising:
a cassette body defining an inlet port, a first reservoir, a second reservoir, a first mixing chamber, and a second mixing chamber;
a first capture disk supported in the body, the capture disk defining a first passage having a first inlet and a first outlet, the first passage housing a first receptor that exhibits specificity for a ligand;
a second capture disk supported in the body, the second capture disk defining a second passage having a second inlet and a second outlet, the second passage housing a second receptor that exhibits specificity for a ligand;
wherein the first capture disk and the second capture disk are rotatable, relative to the body, between a first orientation in which a flow path is formed from the inlet port through the first and second passages, to the first reservoir and a second orientation in which a flow path is formed from the second reservoir, through the first passage, to the first mixing chamber.

18. The assay cassette of claim 17 wherein in the second orientation, a separate flow path is formed from the second reservoir, through the second passage to the second mixing chamber.

19. The assay cassette of claim 17 wherein the flow path in the first orientation is substantially linear.

20. The assay cassette of claim 17 further comprising a first set of generally spherical particles disposed within the first passage and a second set of generally spherical particles, disposed within the second passage, wherein the first set of generally spherical particles are coated with the first receptor and the second set of generally spherical particles are coated with the second receptor.

21. The assay cassette of claim 20 wherein the first set of generally spherical particles and the second set of generally spherical particles are magnetic, and wherein an electromagnet is positioned to anchor the generally spherical particles within their respective passages when the electromagnet is activated.

22. The assay cassette of claim 17 wherein the first mixing chamber and the second mixing chamber contain a liquid crystal material.

23. The assay cassette of claim 17 wherein each of the first passage and the second passage have an inlet and an outlet and wherein the first capture disk and the second capture disk are rotatable to a third orientation in which the inlet and outlet of the first passage and the inlet and outlet of the second passage is blocked.

24. The assay cassette of claim 17 further comprising an actuating member adapted to rotate the first capture disk between the first orientation and the second orientation.

25. The assay cassette of claim 24 wherein the actuating member is adapted to rotate the first capture disk and the second capture disk between the first orientation and the second orientation in unison.

26. The assay cassette of claim 24 further comprising a first set of gear teeth associated with the first capture disk and a second set of gear teeth disposed on the actuating member, wherein the second set of gear teeth are adapted to mate with the first set of gear teeth.

27. The assay cassette of claim 17 further comprising a plurality of parallel tubes disposed in the first passage, wherein the plurality of parallel tubes run the length of the passage.

28. A device for purifying and concentrating a sample for use in detecting the presence of a ligand in the sample, comprising:
a body defining an inlet port, an outlet port, a first reservoir, and a second reservoir;
a capture unit supported in the body, the capture unit defining a throughbore housing a receptor that exhibits specificity for a ligand, the capture unit being movable between a first orientation in which the inlet port is in fluid communication with the first reservoir via the throughbore, and a second orientation in which the second reservoir is in fluid communication with the outlet port via the throughbore; and
a second capture unit supported in the body, the second capture unit defining a second throughbore housing a second receptor that exhibits specificity for a ligand, wherein in the first orientation the throughbore of the capture unit is in fluid communication with the second throughbore of the second capture unit and the first reservoir.

29. The device of claim 28 wherein the device is integrated into a self-contained assay cassette.

30. The device of claim 28 further comprising a plurality of generally spherical particles disposed in the throughbore, wherein each generally spherical particle is coated with the receptor.

31. The device of claim 30 wherein the generally spherical particles are magnetic.

32. The device of claim 30 further comprising one or more structures defining a plurality of parallel passages extending the length of the throughbore, wherein the plurality of generally spherical particles are disposed in the plurality of parallel passages.

33. The device of claim 28 wherein the throughbore has an inlet and an outlet, and wherein the capture unit is movable to a third orientation in which the inlet and the outlet are blocked.

34. The device of claim 28 further comprising an actuating member adapted to move the capture unit between the first orientation and the second orientation.

35. The device of claim 1, wherein in the first orientation the passage of the capture unit and the second passage of the second capture unit are in fluid communication with a reservoir.

* * * * *